United States Patent [19]
Coulthard

[11] Patent Number: 5,822,054
[45] Date of Patent: Oct. 13, 1998

[54] SURFACE INSPECTION LIGHTING APPARATUS

[75] Inventor: Martin Coulthard, Chapel Way, St. Annes, Great Britain

[73] Assignee: Surface Inspection Limited, Bristol, United Kingdom

[21] Appl. No.: 836,624
[22] PCT Filed: Nov. 10, 1995
[86] PCT No.: PCT/GB95/02640
 § 371 Date: May 15, 1997
 § 102(e) Date: May 15, 1997
[87] PCT Pub. No.: WO96/16328
 PCT Pub. Date: May 30, 1996

[30] Foreign Application Priority Data

Nov. 17, 1994 [GB] United Kingdom ............ 9423214

[51] Int. Cl.⁶ .................... G01N 21/00; G01B 11/30
[52] U.S. Cl. ................................. 356/237; 356/371
[58] Field of Search ......................... 356/237, 371, 356/430

[56] References Cited

U.S. PATENT DOCUMENTS 4,629,319 12/1986 Clarke et al. ................ 356/237
5,367,378 11/1994 Harding et al. .

FOREIGN PATENT DOCUMENTS

A 4121464 1/1992 Germany.
WO A 8901146 2/1989 WIPO.

*Primary Examiner*—Frank G. Font
*Assistant Examiner*—Amanda Merlino
*Attorney, Agent, or Firm*—Marshall, O'Toole, Gerstein, Murray & Borun

[57] ABSTRACT

Disclosed is a surface inspection lighting apparatus for use in the visual inspection by a human inspector of a reflective surface for surface defects. The apparatus has a region from which light emanates when the apparatus is in use. The intensity of the light emanating from the region varies substantially as an exponential function and as a sinusoidal function of the distance along an imaginary line across the region. The specular reflection of light from the region in a flat, defect free, reflective test surface is perceived by a human inspector to have a substantially sinusoidal intensity distribution.

10 Claims, 4 Drawing Sheets

SURFACE INSPECTION LIGHTING APPARATUS

TECHNICAL FIELD

This invention relates to a lighting apparatus for visual inspection for defects of a reflective surface.

BACKGROUND

A wide range of manufactured products are visually inspected by human inspectors in order to locate and assess surface defects. For effective inspection a surface must be illuminated in such a way that significant defects can be easily seen and distinguished from other features. The characteristics of the light, such as its intensity and direction, strongly affect the inspection performance.

An example of prior art in this field is U.S. Pat. No. 5,237,404, assigned to Mazda Motor Corporation ('the Mazda patent'). This patent is for an automatic inspection system consisting of a light radiation means, an imaging means and a discriminating means. The light from the light radiation means has a 'predetermined change pattern' which is, optionally, such that 'a luminous intensity is gradually changed from a high level to low level along a predetermined direction'.

The present invention is distinct from the Mazda patent in that the present invention is directed exclusively towards human visual inspection, and not towards automatic inspection. The distribution of light from the present invention is specific to human visual inspection, so the present invention would be inappropriate for automatic inspection.

Thus, hitherto, when the paint on car bodies is inspected in order to find defects to be repaired, such as dirt, arrays of fluorescent lamps are typically used as the lighting system. Human inspectors view the reflection of the lamps in the paint in order to see the defects. This technique, however, suffers from a number of drawbacks. The visibility of defects is different at different positions in the field of view, it is difficult to assess the severity of defects and It is hard to distinguish defects which should be repaired from surface features such as orange peel.

The present invention seeks to provide an apparatus which is less subject to these drawbacks.

ESSENTIAL TECHNICAL FEATURES

According to the present invention there is provided a surface inspection lighting apparatus for use in the visual inspection by a human inspector of a reflective test surface for surface defects, having a region from which light emanates when the apparatus is in use, the intensity of the light emanating from the said region varying gradually substantially as an exponential function of a sinusoidal function of the distance along an imaginary line across the said region, so that the specular reflection of light from said region in a flat, defect free, reflective test surface is perceived by a human inspector to have a substantially sinusoidal intensity distribution.

Preferred attributes and features of the invention are described hereafter.

The inspector looks at the specular reflection of the apparatus in the test surface. If the test surface is reflective, smooth and free of defects then the test surface acts as a mirror and the inspector perceives a smooth, sinusoidal intensity distribution and can judge that the surface is of good quality.

A surface defect on a reflective surface typically distorts the level of the surface. Light specularly reflected by the defect is therefore reflected in a direction different from that of the light reflected by the good quality surface that surrounds it. When the inspector views the reflection of the apparatus in the test surface, at the location of the defect he sees light reflected from a position on the apparatus that is remote from the positions on the apparatus from which light is reflected to the inspector by the good quality surface surrounding the defect. As the intensity of the light emanating from the apparatus varies gradually across it, the defect is perceived to have an intensity different to that of its surrounding area. If the severity and size of the defect are sufficient the inspector sees a sharp change in the intensity at the location of the defect and this can be distinguished from the gradual changes in the intensity due to the spatial pattern of the apparatus.

The reasons for the suitability of an exponential function of a sinusoidal function for the light intensity distribution are as follows:

Firstly, it is essential that the light intensity varies across the apparatus for defects to be visible, as described above.

Secondly, the human visual/perceptual system is sensitive both to step changes in light intensity within a field of view, and to step changes in light intensity gradient. A person therefore easily perceives visual features of this kind. On the other hand the visual/perceptual system is relatively insensitive to slow, gradual changes of intensity or intensity gradient, so a person does not readily perceive features of these kinds. In signal processing terms, it appears that the human eye/brain system carries out a kind of automatic filtering operation that passes features of high spatial frequency and allows them to be perceived, but cuts out low spatial frequency features so that they are generally ignored.

A pattern of light with a sinusoidal distribution of intensity has neither sharp intensity changes nor sharp changes in intensity gradient (nor, indeed, sharp changes in any higher order differentials). Such a pattern, with a sufficiently long wavelength of sine wave, is therefore effectively 'filtered out' by the human perception system, allowing attention to be readily given to small features corresponding to surface defects.

Thirdly, research has shown that the intensity of light perceived by a human is substantially a logarithmic function of the actual light intensity. For example a person judges a small change in a low light intensity to be of similar magnitude to a large change in a high light intensity. For a light distribution to be perceived as sinusoidal, therefore, the actual light distribution should be an exponential function of a sine wave, so that the exponential function acts as the inverse of the logarithmic perception function.

A light distribution which approximates well to the ideal distribution described above can be produced by one or more light source(s) covered with a diffuser panel. The light emanating from the diffuser panel is made to conform to the required light distribution by masking it with a computer generated printed pattern, applied on the side of the apparatus facing away from the light source(s).

The spatial pattern of light intensity can take a number of forms. Preferably the pattern is in the form of linear, parallel, alternating dark and bright bands. Alternatively the distribution can be a pattern of tiled, or tessellated, polygons such as triangles, squares or hexagons. In each case, however, the distribution of light intensity across the band or tile is an exponential function of a sinusoidal function of the distance across the said region.

The apparatus can advantageously be used for the visual inspection of painted vehicle bodies for paint and other defects. In this application a number of units of the apparatus may be configured as a planar array. A vertical array may form a wall, while a generally horizontal array may form a ceiling.

On a car body paint inspection line it is preferred to use two wall arrays to provide coverage of the entire vehicle.

These walls are typically positioned facing each other, on opposite sides of the vehicle body under inspection.

Where this provides insufficient coverage a generally horizontal ceiling array may be added to form an arch, or positioned separately as a stand alone array.

Depending on the application, the arrays can also be configured to give a wall on its own, or a single wall in conjunction with a ceiling array. A ceiling array alone could be employed where inspection is for generally horizontal surfaces only.

EXAMPLE

An example of apparatus embodying the present invention, configured for visual inspection of vehicle paintwork by a human inspector, will now be described with reference to the accompanying drawings in which.

Figure 1:
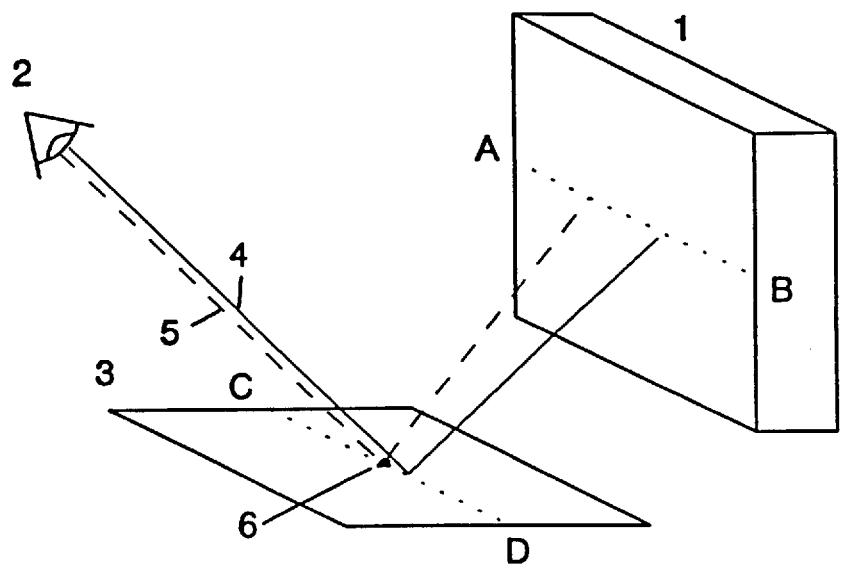
FIG. 1 is a diagram showing the general arrangement of the apparatus, the painted surface and the inspector.

The apparatus is a light box with a diffuser panel over its front and a printed pattern applied to the front of the diffuser. As shown in FIG. 1, the light box 1 is positioned such that the eye of the inspector 2 sees the specular reflection of the light box in the painted surface 3. The painted surface can, for example, be part of the bonnet of a painted car body. One of the light paths 4 from the light box to the inspector via a good quality area of the painted surface is shown as a solid line. A light path 5, from the light box to the inspector via a defect 6, is shown as a dashed line. This illustrates how light is deflected by the defect. At the defect the inspector sees reflected light from a part of the light pattern remote from that part of the light pattern from which light is seen by the inspector reflected in the good quality surface adjacent to the defect. An imaginary line A–B is shown across the front of the light box, and a second imaginary line C–D is shown across the painted surface, passing through the defect.

Figure 2:
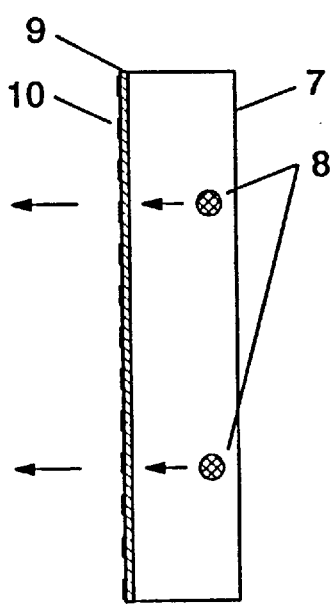
FIG. 2 is a simplified cross-section of the apparatus, the view being that of an horizontal slice through the unit at the position of the line A–B.

FIG. 2 shows a horizontal cross-section of the light box through the line A–B. The light box comprises an open fronted box 7 in which is mounted one or more vertical parallel white fluorescent lamp(s) 8. A white acrylic diffuser panel 9 is fixed over the front of the box and in front of the diffuser is a mask, in the form of a sheet 10 of transparent plastics material, for example polyester, onto which is printed a computer generated pattern. This pattern comprises a myriad of black dots of varying sizes on unprinted background, or black print with a myriad of dots of varying sizes where there is no print, as with black and white printed graphical newspaper images. The density of the print is an approximation to the exponential of a sinusoidal distribution, weighted to account for the natural distribution of light from the lamp(s) through the diffuser.

At the parts of the diffuser panel closest to the lamp(s) the intensity of light produced is high. At other points across the front of the apparatus the light intensity is reduced both by the greater distance from the lamps and the effect of the masking pattern.

This produces a pattern of parallel bands, the intensity of the light across which changes gradually from dark to bright and back to dark.

Figure 3:
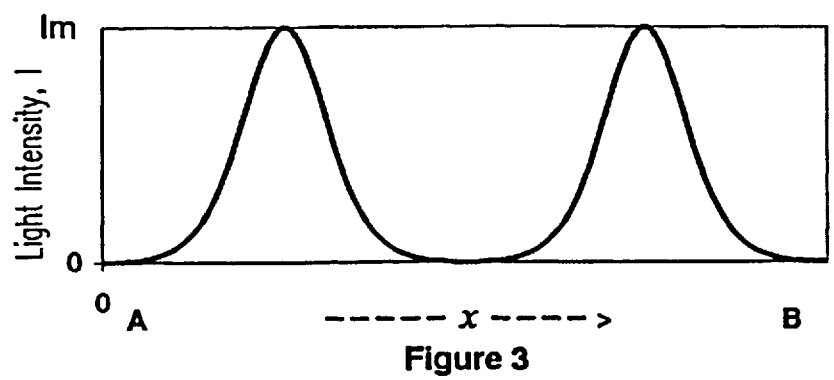
FIG. 3 is a graph of the intensity of light emanating from the apparatus along an imaginary line A–B across the centre of the apparatus.

Selection of suitable components, printed pattern and geometry for the light box produces a light intensity distribution which is an exponential function of a sinusoidal function of the distance along the line A–B, as shown in FIG. 3.

Figure 4:
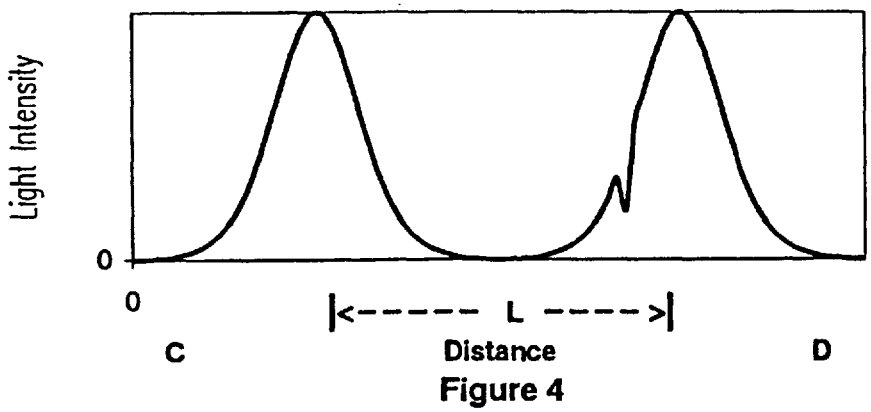
FIG. 4 is a graph of the intensity of light from the apparatus after reflection by a painted surface, along an imaginary line C–D across the painted surface passing through a defect.

The equation for the light intensity I, as a function of the distance x along the line A–B, is:

$$I = \left(\frac{b}{R}\right) \cdot \left[\left[\exp\left\{\left[\frac{Im \cdot R}{2 \cdot a}\right] \cdot \left[1 - \cos\left(\frac{2 \cdot PI \cdot x}{L}\right)\right]\right\} - 1\right]\right] \quad (1)$$

where:
exp indicates the exponential function (e raised to the power of . . . );
I=light intensity;
b=a constant derived from the response of the human visual system to light intensity, equal to 0.5 for this example;
R=reflectivity of the paint (,the proportion of incident light that is specularly reflected), equal to 0.1 for this example;
Im=maximum light intensity (as indicated in FIG. 3);
PI=ratio of the circumference of a circle to the length of its diameter;
L=wavelength (distance between centres of adjacent bright bands, as indicated in FIG. 4); and $$a = \frac{Im \cdot R}{\ln\left[\left(\frac{Im \cdot R}{b}\right) + 1\right]} \quad (2)$$

The equation for the density of the print of the printed pattern which achieves this, also as a function of the distance x along the line A–B, duly weighted to account for the natural distribution of light from the lamp(s) through the unmasked diffuser is:

$$D = 1 - \left(\frac{I}{In}\right) \quad (3)$$

Where:
D=density of the print of the printed pattern, which has the value 1 where it gives a 100% coverage of a given area and the value 0 where it is completely absent from a given area;

I=desired light intensity distribution according to equation 1; and

In=natural light distribution of the light source through the unmasked diffuser, measured empirically by scanning a light meter across the front surface of the unmasked diffuser.

The light intensity I as a function of distance x along the line A–B is a wave-like distribution in which the light intensity changes smoothly between dark and bright. The distribution is weighted towards the dark, i.e. the majority of the width of the distribution is less than half the maximum intensity. The light intensity at the darkest parts of the distribution is substantially zero. The light intensity at the points half way between the centres of adjacent bright and dark bands is substantially 12% of the maximum intensity.

When the inspector views the line A–B reflected in the line C–D across the painted surface his eye receives light with the intensity distribution shown in FIG. 4. There is a sharp change in light intensity at the location of the defect due to deflection of light by the defect.

Figure 5:
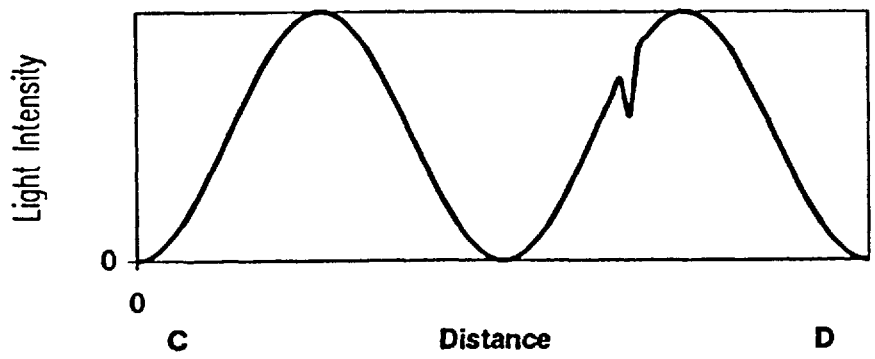
FIG. 5 is a graph of the intensity of light from the apparatus after reflection by a painted surface, along an imaginary line C–D across the painted surface passing through a defect, as it is perceived by the inspector.

As previously described, the light intensity that is perceived by the human eye/brain system is a logarithmic function of the actual intensity of light arriving at the eye. The distribution of light perceived by the inspector along line C–D, shown in FIG. 5, is modified from the actual distribution by a logarithmic function. The inspector therefore perceives a sinusoidal light distribution, with gently changing light intensity, except at the location of the defect, where he sees a sharp change in brightness. He can therefore readily identify the defect.

Variations on the pattern shown in FIG. 3 can be used to give the desired results, in terms of the visibility of specific defect types. In particular, if the pattern wavelength L (the distance from the centre of a bright band to the centre of the adjacent bright band) of the pattern is short in relation to the distance of the light box from the painted surface, defects of low severity are visible.

More typically for the inspection of paint a longer pattern wavelength is used in order that low severity defects, such as orange peel, are not visible, while more severe defects like dirt can clearly be seen. This means that only the defects which can and should be repaired are visible, so that the amount of visual information is reduced and the inspector can carry out his task more effectively.

Within a certain range of defect severity (dependent on the ratio of the pattern wavelength to the offset of the apparatus from the painted surface) defects of greater severity appear to have greater contrast, and can therefore be distinguished from defects of lower severity. This facilitates the inspector's decision of whether a defect is severe enough to need to be repaired.

Figure 6:
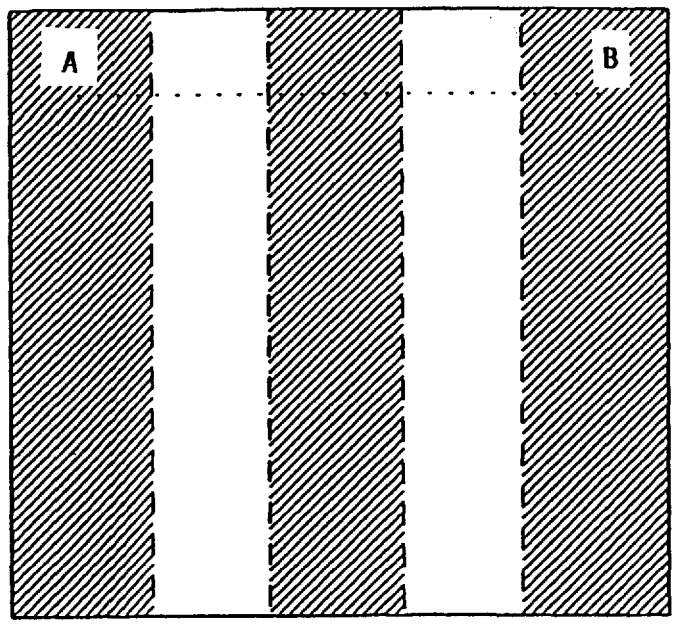
FIG. 6 is an illustration of the front of the apparatus with a linear, parallel pattern of intensity bands.
Figure 7:
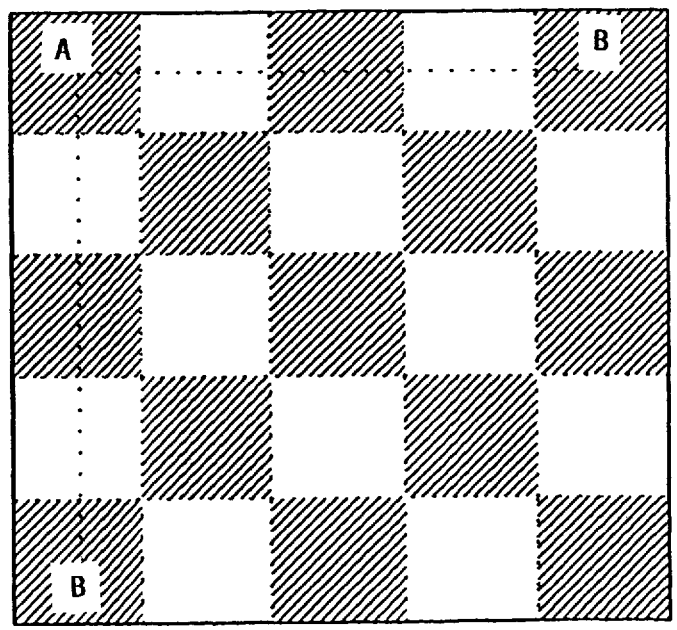
FIG. 7 is an illustration of the front of the apparatus with a tessellated squares pattern of intensities.

As an alternative to linear bands on the front of the light box, as shown in FIG. 6, a pattern of tessellated squares can be used, as shown in FIG. 7. In both figures the hatched parts of the diagram indicate the areas that appear dark, while the unhatched parts are those areas that appear bright. The hatching itself is not part of the pattern. The distribution of light along the imaginary line A–B shown in each of FIGS. 1, 6 and 7 is as shown in FIG. 3.

Figure 8:
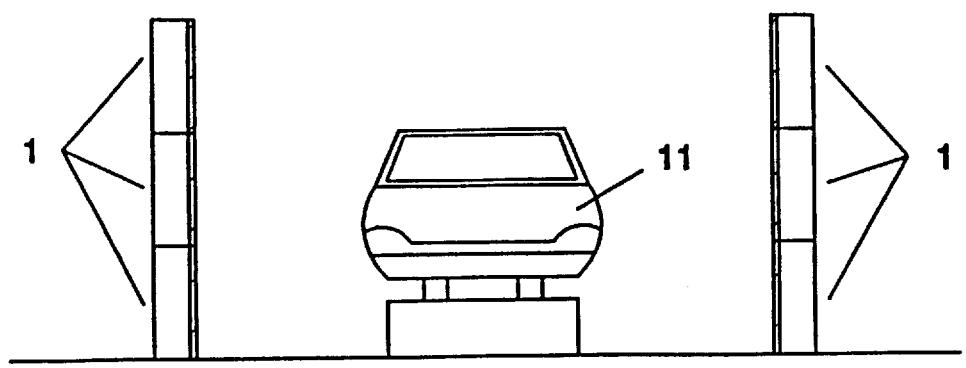
FIG. 8 is the view of a number of light boxes each constituting such apparatus, configured for car body paint inspection. The front of the car and the sides of the light boxes are shown.

An example of the configuration of the apparatus for the inspection of a painted car body is shown in FIG. 8. Multiple light boxes 1 are stacked to form two vertical arrays, each three light boxes high. The arrays can also be extended in the horizontal direction, parallel to the side of the car body, to give additional coverage along the length of the car body. The arrays are positioned respectively on opposite sides of the car body 11 to be inspected, with the light emanating surfaces facing each other. The inspector stands between the wall and the car body, viewing the reflection of the walls in the surface of the painted car body.

I claim:

1. Surface inspection lighting apparatus for use in a visual inspection by a human inspector of a reflective surface for surface defects, having a region from which light emanates when the apparatus is in use, the intensity of the light emanating from the said region varying as an exponential function of a sinusoidal function of the distance along an imaginary line across the said region, so that the specular reflection of light from the said region in a flat, defect free, reflective test surface is perceived by a human inspector to have a substantially sinusoidal intensity distribution.

2. An apparatus according to claim 1, in which the intensity of the light emanating from the region as a function of the distance along an imaginary line across the region is given by the equation:

$$I = \left(\frac{b}{R}\right) \cdot \left[\left[\exp\left\{\left[\frac{Im \cdot R}{2 \cdot a}\right] \cdot \left[1 - \cos\left(\frac{2 \cdot PI \cdot x}{L}\right)\right]\right\} - 1\right]\right]$$

where:
exp indicates the exponential function;
I=light intensity;
b=a constant derived from the response of a human visual system to light intensity;
R=reflectivity of the surface i.e. the proportion of incident light that is specularly reflected;
Im=maximum light intensity;
PI=ratio of the circumference of a circle to the length of its diameter;
L=wavelength i.e. distance between centres of adjacent bright bands;
x=distance from an edge of the apparatus along an imaginary line across the region and $$a = \frac{Im \cdot R}{\ln\left[\left(\frac{Im \cdot R}{b}\right) + 1\right]}$$

3. An apparatus according to claim 1, in which the variation of intensity of light emanating from the region has a spatial pattern which is in the form of linear, parallel alternating light and dark bands.

4. An apparatus according to claim 1, in which the variation of intensity of light emanating from the region has a spatial pattern which is in the form of tessellated polygons.

5. An apparatus according to claim 1, in which light is produced by one or more light source(s), is diffused by a diffuser panel and is subsequently partially masked by a printed pattern.

6. An apparatus according to claim 5, in which the density of the print of the printed pattern as a function of the distance along an imaginary line across the said region is given by the equation:

$$D = 1 - \left(\frac{I}{In}\right)$$

Where:
D=density of the print of the printed pattern;
I=the light intensity distribution as set out in claim 2;

In=natural light intensity distribution of the light source through an unmasked diffuser, measured empirically by scanning a light meter across the front surface of the unmasked diffuser.

7. Apparatus according to claim 1, assembled together to form one or more planar array(s) in any one of the following configurations: single wall, single wall and ceiling, ceiling only, two walls opposite and facing each other, two walls opposite and facing each other with a ceiling above them.

8. Apparatus according to claim 1 for use in the visual inspection of painted vehicle bodies or panels.

9. A mask bearing a printed pattern suitable for a surface inspection lighting apparatus for use in a visual inspection of a reflective surface for surface defects, and in which light is produced by one or more light sources, is diffused by a diffuser panel and is subsequently partially masked by a printed pattern to provide a region from which light emanates when the apparatus is in use, the intensity of the light emanating from said region varying as an exponential function of a sinusoidal function of the distance along an imaginary line across said region so that the specular reflection of light from said region in a flat, defect free, reflective test surface is perceived by a human inspector to have a substantially sinusoidal intensity distribution.

10. A mask according to claim 9, in which the intensity of the printed pattern varies as a function of the distance along an imaginary line across the region and is given by the equation:

$$D = 1 - \left( \frac{I}{In} \right)$$

Where:

D=density of the print of the printed pattern;

In=natural light intensity distribution of the light source through a unmasked diffuser, measured empirically by scanning a light meter across the from surface of the unmasked diffuser, and $$I = \left( \frac{b}{R} \right) \cdot \left[ \left[ \exp\left\{ \left[ \frac{Im \cdot R}{2 \cdot a} \right] \cdot \left[ 1 - \cos\left( \frac{2 \cdot PI \cdot x}{L} \right) \right] \right\} - 1 \right] \right]$$

where:

exp indicates the exponential function;

I=light intensity;

b=a constant derived from the response of a human visual system to light intensity;

R=reflectivity of the surface i.e., the proportion of incident light that is specularly reflected;

Im=maximum light intensity;

PI=ratio of the circumference of a circle to the length of its diameter;

L=wavelength i.e., distance between centres of adjacent bright bands;

x=distance from an edge of the apparatus along an imaginary line across the region and $$a = \frac{Im \cdot R}{\ln\left[ \left( \frac{Im \cdot R}{b} \right) + 1 \right]}$$

* * * * *